United States Patent [19]
Rosen et al.

[11] Patent Number: 5,491,246
[45] Date of Patent: Feb. 13, 1996

[54] SYNTHESIS OF GROUP 4 METAL DIENE COMPLEXES

[75] Inventors: Robert K. Rosen, Sugarland, Tex.; David D. Devore, Midland, Mich.

[73] Assignee: The Dow Chemical Company, Midland, Mich.

[21] Appl. No.: 427,378

[22] Filed: Apr. 24, 1995

[51] Int. Cl.$^6$ .............. C07F 17/00; C07F 7/00; C07F 7/28

[52] U.S. Cl. .............. 556/7; 556/11; 556/12; 556/14; 556/19; 556/28; 556/52; 556/56

[58] Field of Search ............ 556/7, 11, 12, 556/14, 19, 28, 52, 56

[56] References Cited

U.S. PATENT DOCUMENTS

| | | | |
|---|---|---|---|
| 5,055,438 | 10/1991 | Canich | 502/117 |
| 5,057,475 | 10/1991 | Canich et al. | 502/104 |
| 5,064,802 | 11/1991 | Stevens et al. | 502/155 |
| 5,096,867 | 3/1992 | Canich | 502/103 |
| 5,132,380 | 7/1992 | Stevens et al. | 526/126 |
| 5,153,157 | 10/1992 | Hlatky et al. | 502/117 |
| 5,198,401 | 3/1993 | Turner et al. | 502/155 |
| 5,372,682 | 12/1994 | Devore et al. | 204/72 |

FOREIGN PATENT DOCUMENTS

| | | |
|---|---|---|
| 9319104 | 9/1993 | WIPO . |
| WO9500526 | 7/1995 | WIPO . |

OTHER PUBLICATIONS

J. Blenkers, et al. *Organometallics*, 1987, 6 459–469.
H. Yasuda, et al. *Acc. Chem. Res.*, 1985, 18, 120–126.
H. Yasuda, et al. *Organometallics*, 1982, 1, 388–396.

*Primary Examiner*—Porfirio Nazario-Gonzales

[57] ABSTRACT

A process for preparing titanium or zirconium diene complexes wherein the metal is in the +2 formal oxidation state comprising contacting a conjugated or nonconjugated $C_{4-40}$ diene compound with a hydrocarbyloxide containing precursor complex.

4 Claims, No Drawings

SYNTHESIS OF GROUP 4 METAL DIENE COMPLEXES

BACKGROUND OF THE INVENTION

The present invention relates to a process for preparing certain coordination complexes of Group 4 metals in the +2 formal oxidation state starting from hydrocarbyloxide compounds wherein the metal is in the +or +4 formal oxidation state. The metal complexes are highly useful as components of addition polymerization catalysts used to prepare polyolefins.

In WO 95-00526 the preparation of certain titanium and zirconium complexes comprising a single, cyclic, delocalized Π-bonded ligand group wherein the metal of said complexes is in the +2 formal oxidation state from the corresponding metal halides is disclosed.

The above mentioned synthetic method to prepare the metal coordination complexes use metal halide compounds as starting materials, which are corrosive, toxic, and air and moisture sensitive. In order to facilitate handling thereof, the halide compound is typically converted to its ether-adduct in a separate step with for example THF or diethyl ether. This adduct formation step often proceeds with difficulty, requiring reduced temperatures and an inert atmosphere. For this and other reasons, the resulting yield of the aforementioned preparation is undesirably low.

SUMMARY OF THE INVENTION

According to the present invention there is provided a process for preparing a metal complex corresponding to the formula:

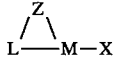

wherein:
M is titanium or zirconium in the +2 formal oxidation state;
L is a group containing a cyclic, delocalized, anionic, Π-system through which the group is bound to M;
Z is a divalent moiety bound to both L and M comprising boron, or a member of Group 14 of the Periodic Table of the Elements, and also comprising nitrogen, phosphorus, sulfur or oxygen, said moiety having up to 60 non-hydrogen atoms; and
X is a neutral, conjugated or nonconjugated diene, optionally substituted with one or more hydrocarbyl groups, said X having up to 40 carbon atoms and forming a Π-complex with M;
the steps of the process comprising:
1)
a) contacting a conjugated or nonconjugated $C_{4-40}$ diene compound with a metal complex corresponding to the formula:

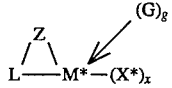

wherein,
M* is titanium or zirconium in the +or +4 formal oxidation state;
X* independently each occurrence is a $C_{1-20}$ hydrocarbyloxide;
x is one or two;
G is a neutral Lewis base selected from amines, phosphines and ethers said G having from 3 to 20 non-hydrogen atoms;
L and Z are as previously defined; and
g is a number from 0 to 3,
in an inert solvent, and
b) contacting the resulting mixture with a reducing agent, or
2)
a) contacting a conjugated or nonconjugated $C_{4-40}$ diene compound with a reducing agent in a suitable noninterfering solvent, and
b) contacting the resulting mixture with a complex corresponding to the formula:

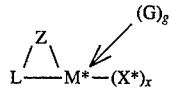

wherein,
L, Z, M*, X*, x, G and g are as previously defined.

It has been found that hydrocarbyloxy groups on the metal center of the starting reactants can be readily removed by contacting the starting compound with the diene in the presence of a reducing agent to give the desired complex in high yield and high purity. This discovery is considered to be surprising as hydrocarbyloxy-transition metal bonds are generally stronger bonds than halogen-transition metal bonds and therefore hydrocarbyloxy groups are usually less suitable leaving groups than halogen groups. This has not proven to be true in the present invention which provides the complexes in yields of 90 percent and higher. The product complexes can be readily isolated in high purity by standard filtration techniques. In addition, the starting hydrocarbyloxy compounds are also much less air sensitive, less toxic, and are more readily soluble in hydrocarbons than are the corresponding halide compounds, making the present invention more desirable for commercial implementation.

DETAILED DESCRIPTION OF THE INVENTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering Groups.

It is understood that the bonds between the metal atom and each constituent atom of the Π-bonded moiety need not be equivalent. That is, the metal may be symmetrically or unsymmetrically Π-bound to L.

The metal hydrocarbyloxy complexes used as starting reactants in the present invention may be prepared by contacting a metal hydrocarbyloxy compound of the formula:

wherein,
M* and X* are as previously defined; and
x' is 3 or 4, with a dianionic salt compound of the formula:

(D)₂(L—Z)

wherein:
D independently each occurrence is a Group 1 metal or a Group 2 metal monohalide, and
L and Z are as previously defined.

Preferably, X* independently each occurrence is selected from the group consisting of alkoxy, aryloxy, alkaryloxy, and arylalkoxy groups, said X* having up to 10 carbons, more preferably X* each occurrence is independently selected from the group consisting of methoxy, ethoxy, isopropoxy, n-butoxy, and t-butoxy.

A neutral Lewis base, G, such as an ether or amine compound, may also be associated with the complex, if desired, however, such is generally not preferred.

Preferred metal coordination complexes prepared in the present process are those compounds of the formula:

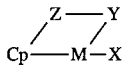

wherein;
M and X are as previously defined;
Cp is a $C_5H_4$ group bound to Z and bound in an η5 bonding mode to M or is such an $\eta^5$ bound group substituted with from one to four substituents independently selected from hydrocarbyl, silyl, germyl, halo, cyano, and combinations thereof, said substituent having up to 20 nonhydrogen atoms, and optionally, two such adjacent substituents are joined together causing Cp to have a fused ring structure;
Z is $SiR^*_2$, $CR^*_2$, $SiR^*_2SiR^*_2$, $CR^*_2CR^*_2$, $CR^*=CR^*$, $CR^*_2SiR^*_2$, $GeR^*2$, $BR^*$, or $BR^*2$, wherein R* each occurrence is independently selected from the group consisting of hydrogen, hydrocarbyl, halogenated hydrocarbyl, and silyl groups having up to 20 non-hydrogen atoms, and mixtures thereof, or two or more R* groups from Z, or an R* group from Z together with Y form a fused ring system; and
Y is a divalent anionic ligand group comprising nitrogen, phosphorus, oxygen or sulfur and having up to 20 non-hydrogen atoms, said Y being bonded to Z and M through said nitrogen, phosphorus, oxygen or sulfur.

Further preferably, Y is —O—, —S—, —NR*—, or —PR*— wherein R* is as previously defined. Highly preferably Y is a nitrogen or phosphorus containing group corresponding to the formula—N(R")—or—P(R")—, wherein R" is $C_{1-10}$ hydrocarbyl.

Further preferred Cp groups include cyclopentadienyl, indenyl, tetrahydroindenyl, fluorenyl, tetrahydrofluorenyl, octahydrofluorenyl groups, and such groups substituted with from one to eight substituents of up to 20 nonhydrogen atoms per substituent.

More preferably, hydrocarbyloxy complexes used in the present process correspond to the formula:

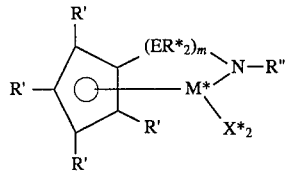

and the resulting diene containing products correspond to the formula:

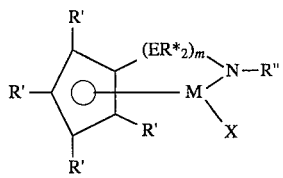

wherein:
M, M*, R", X* and X are as previously defined;
R" each occurrence is independently selected from the group consisting of hydrogen, silyl, alkyl, aryl, germyl, cyano, halo and combinations thereof having up to 20 non-hydrogen atoms, or two R" groups together form a divalent derivative thereof;
R* each occurrence is independently selected from the group consisting of hydrocarbyl, halohydrocarbyl, and silyl groups having up to 20 non-hydrogen atoms, and mixtures thereof;
E is silicon or carbon; and
m is 1 or 2.

Most highly preferred metal diene complexes are titanium compounds wherein $(ER^*_2)m$ is dimethylsilyl or 1,2-ethanediyl, R" is methyl, ethyl, propyl, butyl, pentyl, hexyl, (including all isomers where applicable), norbornyl, benzyl, or phenyl; L is cyclopentadienyl, indenyl, tetrahydroindenyl, fluorenyl, tetrahydrofluorenyl, octahydrofluorenyl, or a methyl substituted derivative thereof; and X is 1,4-diphenyl-1,3-butadiene, 1,3-pentadiene, 1,4-dibenzyl-1,3-butadiene, 2,4-hexadiene, 3-methyl-1,3-pentadiene, 1,4-ditolyl-1,3-butadiene, or 1,4-bis(trimethylsilyl)-1,3-butadiene.

Specific highly preferred titanium hydrocarbyloxy coordination compounds used as starting reactants include: (tert-butylamido)(tetramethyl-$\eta^5$-cyclopentadienyl)-1,2-ethanediyltitanium diethoxide, (tert-butylamido)(tetramethyl-$\eta^5$-cyclopentadienyl)-1,2-ethanediyltitanium diisopropoxide, (tert-butylamido)(tetramethyl-$\eta^5$-cyclopentadienyl)-1,2-ethanediyltitanium di-n-butoxide, (tert-butylamido)(tetramethyl-$\eta^5$-cyclopentadienyl)dimethylsilanetitanium diethoxide, (tert-butylamido)(tetramethyl-$\eta^5$-cyclopentadienyl)dimethylsilanetitanium diisopropoxide, (tert-butylamido) (tetramethyl-$\eta^5$-cyclopentadienyl)dimethilsilanetitanium di-n-butoxide, (methylamido)(tetramethyl-$\eta^5$-cyclopentadienyl)dimethylsilanetitanium diethoxide, (methylamido)(tetramethyl-$\eta^5$-cyclopentadienyl)dimethylsilanetitanium diisopropoxide, (methylamido)(tetramethyl$\eta^5$-cyclopentadienyl)dimethylsilanetitanium di-n-butoxide, (phenylamido)(tetramethyl-$\eta^5$-cyclopentadienyl)dimethylsilanetitanium diethoxide, (phenylamido)(tetramethyl-$\eta^5$-cyclopentadienyl)dimethylsilanetitanium diisopropoxide, (phenylamido)(tetramethyl-$\eta^5$-cyclopentadienyl)dimethylsilanetitanium di-n-butoxide, (benzylamido)(tetramethyl-$\eta^5$-cyclopentadienyl)dimethylsilanetitanium diethoxide, (benzylamido)(tetramethyl-$\eta^5$-cyclopentadienyl)dimethylsilanetitanium diisopropoxide, (benzylamido)(tetramethyl-$\eta^5$-cyclopentadienyl)dimethylsilanetitanium di-n-butoxide, (tert-butylamido)($\eta^5$-cyclopentadienyl)-1,2-ethanediyltitanium diisopropoxide, (tert-butylamido)(η5-cyclopentadienyl)1,2-ethanediyltitanium di-n-butoxide, (tert-butylamido)($\eta^5$-cyclopentadienyl)dimethylsilanetitanium diisopropoxide, (tert-butylamido)($\eta^5$-cyclopentadienyl)dimethylsilanetitanium di-n-butoxide, (methylamido)($\eta^5$-cyclopentadienyl)dimethylsilanetitanium diisopropoxide, (t-butylamido)($\eta^5$- cyclopentadienyl)dimethylsilanetitanium di-n-butoxide, (t-butylamido)indenyldimethylsilanetitanium diisopropoxide, (t-butylamido)indenyldimethylsilanetitanium di-n-butoxide, and (benzylamido)indenyldimethylsilanetitanium diisopropoxide.

Specific highly preferred titanium (II) diene complexes include: (tert-butylamido)(tetramethyl-$\eta^5$-cyclopentadienyl)-1,2-ethanediyltitanium 1,4-diphenyl-1,3-butadiene, (tert-butylamido)(tetramethyl-$\eta^5$-cyclopentadienyl)dimethylsilanetitanium 1,4-diphenyl-1,3-butadiene, (methylamido)(tetramethyl-$\eta^5$-cyclopentadienyl)dimethylsilanetitanium 1,4-diphenyl-1,3-butadiene, (phenylamido)(tetramethyl-$\eta^5$-cyclopentadienyl)dimethylsilanetitanium 1,4-diphenyl-1,3-butadiene, (benzylamido)(tetramethyl-$\eta^5$-cyclopentadienyl)dimethylsilanetitanium 1,4-diphenyl-1,3-butadiene, (tert-butylamido)($\eta^5$-cyclopentadienyl)-1,2-ethanediyltitanium 1,4-diphenyl-1,3-butadiene, (tert-butylamido)($\eta^5$-cyclopentadienyl)dimethylsilanetitanium 1,4-diphenyl-1,3-butadiene, (methylamido)($\eta$5-cyclopentadienyl)dimethylsilanetitanium 1,4-diphenyl-1,3-butadiene, (t-butylamido)indenyldimethylsilanetitanium 1,4-diphenyl-1,3-butadiene, (benzylamido)indenyldimethylsilanetitanium 1,4-diphenyl-1,3-butadiene, (tert-butylamido)(tetramethyl-$\eta^5$-cyclopentadienyl)1,2-ethanediyltitanium 1,3-pentadiene, (tert-butylamido)(tetramethyl-$\eta^5$-cyclopentadienyl)dimethylsilanetitanium 1,3-pentadiene, (methylamido)(tetramethyl-$\eta^5$-cyclopentadienyl)dimethylsilanetitanium 1,3-pentadiene, (phenylamido)(tetramethyl-$\eta^5$-cyclopentadienyl)dimethylsilanetitanium 1,3-pentadiene, (benzylamido)(tetramethyl-$\eta^5$-cyclopentadienyl)dimethylsilanetitanium 1,3-pentadiene, (tert-butylamido)($\eta^5$-cyclopentadienyl)-1,2-ethanediyltitanium 1,3-pentadiene, (tert-butylamido)($\eta^5$-cyclopentadienyl)dimethylsilanetitanium 1,3-pentadiene, (methylamido)($\eta^5$-cyclopentadienyl)dimethylsilanetitanium 1,3-pentadiene, (t-butylamido)indenyldimethylsilanetitanium 1,3-pentadiene, (benzylamido)indenyldimethylsilanetitanium 1,3-pentadiene, (tert-butylamido)(tetramethyl-$\eta^5$-cyclopentadienyl)-1,2-ethanediyltitanium 1,4-dibenzyl-1,3-butadiene, (tert-butylamido)(tetramethyl-$\eta^5$-cyclopentadienyl)dimethylsilanetitanium 1,4-dibenzyl-1,3-butadiene, (methylamido)(tetramethyl-$\eta^5$-cyclopentadienyl)dimethylsilanetitanium 1,4-dibenzyl-1,3-butadiene, (phenylamido)(tetramethyl-$\eta^5$-cyclopentadienyl)dimethylsilanetitanium 1,4-dibenzyl-1,3-butadiene, (benzylamido)(tetramethyl-$\eta^5$-cyclopentadienyl)dimethylsilanetitanium 1,4-dibenzyl-1,3-butadiene, (tert-butylamido)($\eta^5$-cyclopentadienyl)-1,2-ethanediyltitanium 1,4-dibenzyl-1,3-butadiene, (tert-butylamido)($\eta^5$-cyclopentadienyl)dimethylsilanetitanium 1,4-dibenzyl-1,3-butadiene, (methylamido)($\eta^5$-cyclopentadienyl)dimethylsilanetitanium 1,4-dibenzyl-1,3-butadiene, (t-butylamido)indenyldimethylsilanetitanium 1,4-dibenzyl-1,3-butadiene, (benzylamido)indenyldimethylsilanetitanium 1,4-dibenzyl-1,3-butadiene, (tert-butylamido)(tetramethyl-$\eta^5$-cyclopentadienyl)-1,2-ethanediyltitanium 2,4-hexadiene, (tert-butylamido)(tetramethyl-$\eta^5$-cyclopentadienyl)dimethylsilanetitanium 2,4-hexadiene, (methylamido)(tetramethyl-$\eta^5$-cyclopentadienyl)dimethylsilanetitanium 2,4-hexadiene, (phenylamido)(tetramethyl-$\eta^5$-cyclopentadienyl)dimethylsilanetitanium 2,4-hexadiene, (benzylamido)(tetramethyl-$\eta^5$-cyclopentadienyl)dimethylsilanetitanium 2,4-hexadiene, (tert-butylamido)($\eta^5$-cyclopentadienyl)-1,2-ethanediyltitanium 2,4-hexadiene, (tert-butylamido)($\eta^5$-cyclopentadienyl)dimethylsilanetitanium 2,4-hexadiene, (methylamido)($\eta^5$-cyclopentadienyl)dimethylsilanetitanium 2,4-hexadiene, (t-butylamido)indenyldimethylsilanetitanium 2,4-hexadiene, (benzylamido)indenyldimethylsilanetitanium 2,4-hexadiene, (tert-butylamido)(tetramethyl-$\eta^5$-cyclopentadienyl)-2-ethanediyltitanium 3-methyl-1,3-pentadiene, (tert-butylamido)(tetramethyl-$\eta^5$-cyclopentadienyl)dimethylsilanetitanium 3-methyl-1,3-pentadiene, (methylamido)(tetramethyl-$\eta^5$-cyclopentadienyl)dimethylsilanetitanium 3-methyl-3-pentadiene, (phenylamido)(tetramethyl-$\eta^5$-cyclopentadienyl)dimethylsilanetitanium 3-methyl-1,3-pentadiene, (benzylamido)(tetramethyl-$\eta^5$-cyclopentadienyl)dimethylsilanetitanium 3-methyl-3-pentadiene, (tert-butylamido)($\eta^5$-cyclopentadienyl)-1,2-ethanediyltitanium 3-methyl-1,3-pentadiene, (tert-butylamido)($\eta^5$-cyclopentadienyl)dimethylsilanetitanium 3-methyl-1,3-pentadiene, (methylamido)($\eta^5$-cyclopentadienyl)dimethylsilanetitanium 3-methyl-3-pentadiene, (t-butylamido)indenyldimethylsilanetitanium 3methyl-1,3-pentadiene, (benzylamido)indenyldimethylsilanetitanium 3-methyl-l,3-pentadiene, (tert-butylamido)(tetramethyl-$\eta^5$-cyclopentadienyl)-1,2-ethanediyltitanium 1,4-ditolyl-1,3-butadiene, (tert-butylamido)(tetramethyl-$\eta^5$-cyclopentadienyl)dimethylsilanetitanium 1,4-ditolyl-1,3-butadiene, (methylamido)(tetramethyl-$\eta^5$-cyclopentadienyl)dimethylsilanetitanium 1,4-ditolyl-1,3-butadiene, (phenylamido)(tetramethyl-$\eta^5$-cyclopentadienyl)dimethylsilanetitanium 1,4-ditolyl-1,3-butadiene, (benzylamido)(tetramethyl-$\eta^5$-cyclopentadienyl)dimethylsilanetitanium 1,4-ditolyl-3-butadiene, (tert-butylamido)($\eta^5$-cyclopentadienyl)-1,2-ethanediyltitanium 1,4-ditolyl-1,3-butadiene, (tert-butylamido)($\eta^5$-cyclopentadienyl)dimethylsilanetitanium 1,4-ditolyl-1,3-butadiene, (methylamido ) ( $\eta^5$-cyclopentadienyl)dimethylsilanetitanium 1,4-ditolyl-1,3-butadiene, (t-butylamido)indenyldimethylsilanetitanium 1,4-ditolyl-1,3-butadiene, (benzylamido)indenyldimethylsilanetitanium 1,4-ditolyl-3-butadiene, (tert-butylamido)(tetramethyl-$\eta^5$-cyclopentadienyl)-1,2-ethanediyltitanium 1,4-bis(trimethylsilyl)-1,3-butadiene, (tert-butylamido)(tetramethyl-$\eta^5$-cyclopentadienyl)dimethylsilanetitanium 1,4-bis(trimethylsilyl)-1 ,3-butadiene, (methylamido)(tetramethyl-$\eta^5$-cyclopentadienyl)dimethylsilanetitanium 1,4-bis(trimethylsilyl)-1,3-butadiene, (phenylamido)(tetramethyl-$\eta^5$-cyclopentadienyl)dimethylsilanetitanium 1,4-bis(trimethylsilyl)-1,3-butadiene, (benzylamido)(tetramethyl-$\eta^5$-cyclopentadienyl)dimethylsilanetitanium 1,4-bis(trimethylsilyl)-1,3-butadiene, (tert-butylamido)($\eta^5$-cyclopentadienyl)-2-ethanediyltitanium 1,4-bis(trimethylsilyl)-1,3-butadiene, (tert-butylamido)($\eta^5$-cyclopentadienyl)-dimethylsilanetitanium 1,4-bis(trimethylsilyl)-1,3-butadiene, (methylamido)($\eta^5$-cyclopentadienyl)dimethylsilanetitanium 1,4-bis(trimethylsilyl)-1,3-butadiene, (t-butylamido)indenyldimethylsilanetitanium 1,4-bis(trimethylsilyl)-1,3-butadiene, and (benzylamido)indenyldimethylsilanetitanium 1,4-bis(trimethylsilyl)-1,3-butadiene.

The corresponding zirconium complexes will be readily apparent to the skilled artisan and will not be listed here.

By the term "reducing agent" herein is meant a metal or compound (or the product resulting from mixing a diene with such metal or compound) which, when combined with the starting complex causes M* to be reduced from the +or +4 formal oxidation state to the +2 formal oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, trihydrocarbylaluminum compounds and Grignard reagents. Most preferred reducing agents are the alkali metals, alkaline earth metals, trialkylaluminum compounds having from 2 to 8 carbons in each alkyl group and $C_{1-8}$ alkyllithium compounds. An especially preferred reducing agent is triethylaluminum.

In the present process an inert, preferably aprotic organic liquid diluent is used. Suitable examples of such diluents are aliphatic or cycloaliphatic ethers and hydrocarbons. Preferably the hydrocarbon diluent is an aliphatic or cycloaliphatic hydrocarbon having from 5 to 10 carbon atoms. Examples include pentane, hexane, heptane, Isopar E™ (a mixture of isoparaffinic hydrocarbons available from Exxon Chemical Inc.), isooctane, cyclohexane, and methylcyclohexane.

The temperature at which the process is conducted is not critical, but is preferably below the boiling point of the diluent. Preferred temperatures range from 0° C. to 200° C., more preferably from 10° C. to 150° C., and most preferably from 20° to 120° C.

Generally the reactants are contacted under an inert atmosphere for a time from several minutes to several days. The presence of oxygen and moisture are preferably avoided. The reactants can be added in any order. Agitation may be employed if desired.

Catalyst systems prepared from the metal complexes are prepared by combining the diene containing metal coordination complex with one or more activating cocatalysts. Preferably the ratio of the coordination complex and cocatalyst on a molar basis is from about 1:0.1 to about 1:10,000. It will, of course, be appreciated that the catalyst system may also be formed in situ if the components thereof are added directly to the polymerization process and a suitable solvent or diluent, including condensed monomer, is used in said polymerization process. Suitable solvents include toluene, ethylbenzene, alkanes and mixtures thereof. In certain cases the catalysts may be isolated from solution and retained under inert atmosphere prior to use. The catalysts' components are sensitive to both moisture and oxygen and should be handled and transferred in an inert atmosphere such as nitrogen, argon or helium or under vacuum.

Suitable activating cocatalysts include polymeric or oligomeric alumoxanes, especially methylalumoxane, triisobutyl aluminum modified methylalumoxane, or diisobutylalumoxane; strong Lewis acids, such as, $C_{1-30}$ hydrocarbyl substituted Group 13 compounds, especially tri(hydrocarbyl)aluminum- or tri(hydrocarbyl)boron compounds and halogenated derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially ammonium, phosphonium, ferrocenium, carbenium or silylium salts of tetrakis(perfluorophenyl)borate; and combinations of the foregoing activating cocatalysts and techniques. The foregoing activating cocatalysts and activating techniques have been previously taught with respect to different metal complexes in the following references: EP-A-277,003, U.S. Pat. No. 5,153, 157, U.S. Pat. No. 5,064,802, EP-A-468,651 (equivalent to U.S. Ser. No. 07/547,718), EP-A-520,732 (equivalent to U.S. Ser. No. 07/876,268), and WO93/23412 (equivalent to U.S. Ser. Nos. 07/884,966 filed May 1, 1992), the teaching of which are hereby incorporated by reference.

Combinations of strong Lewis acids, especially the combination of a trialkyl aluminum compound having from 1 to 4 carbons in each alkyl group and a halogenated tri(hydrocarbyl)boron compound having from 1 to 10 carbons in each hydrocarbyl group, especially tris(pentafluorophenyl)borane, further combinations of such strong Lewis acid mixtures with a polymeric or oligomeric alumoxane, and combinations of a single strong Lewis acid, especially tris(pentafluorophenyl)borane with a polymeric or oligomeric alumoxane are especially desirable activating cocatalysts.

The polymerization is conducted according to known techniques for Ziegler-Natta or Kaminsky-Sinn type polymerizations. That is, the monomer(s) and catalyst are contacted at a temperature from −30° C. to 250° C., at reduced, elevated or atmospheric pressures. The polymerization is conducted under an inert atmosphere which may be a blanketing gas such as nitrogen, argon, hydrogen, ethylene, etc. or under vacuum. Hydrogen may additionally be utilized in the control of molecular weight through chain termination as is previously known in the art. The catalyst may be used as is or supported on a suitable support such as alumina, $MgCl_2$ or silica to provide a heterogeneous supported catalyst. A solvent may be employed if desired. Suitable solvents include toluene, ethylbenzene, alkanes and excess vinyl aromatic or olefin monomer. The reaction may also be conducted under solution or slurry conditions, in a suspension utilizing a perfluorinated hydrocarbon or similar liquid, in the gas phase, i.e. utilizing a fluidized bed reactor, or in a solid phase powder polymerization. A catalytically effective amount of the present catalyst and cocatalyst are any amounts that successfully result in formation of polymer. Such amounts may be readily determined by the routine experimentation by the skilled artisan. Preferred amounts of catalyst and cocatalyst are sufficient to provide an equivalent ratio of addition polymerizable monomer:catalyst of from $1\times10^{10}$:1 to 100:1, preferably from $1\times10^8$:1 to 500:1, most preferably $1\times10^6$:1 to 1000:1. The cocatalyst is generally utilized in an amount to provide an equivalent ratio of cocatalyst:catalyst from 10,000:1 to 0.1:1, preferably from 1,000:1 to 1:1.

The resulting polymeric product is recovered by filtering or other suitable technique. Additives and adjuvants may be incorporated in the polymers of the present invention in order to provide desirable characteristics. Suitable additives include pigments, UV stabilizers, antioxidants, blowing agents, lubricants, plasticizers, photosensitizers, and mixtures thereof.

Having described the invention, the following examples are provided to further illustrate the same and are not to be construed as limiting.

EXAMPLE 1

A) Preparation of di(chloromagnesium)(tert-butylamido)dimethyl(tetramethyl-$\eta^5$-cyclopentadienyl)silane $[Me_4C_5SiMe_2N^tBu][MgCl]_2(DME)_n$ In a drybox, a 3 L round bottom flask equipped with a stirrer, condenser, and a nitrogen inlet was loaded 500 ml of toluene, followed by 106 g of $Me_4C_5HSiMe_{2NH}{}^tBu$, and then 380 ml of 2.2 M $^iPrMgCl$ in diethyl ether. The mixture was heated, and the ether removed by distillation and trapped in a condenser cooled to −78° C. After five hours of heating, heating was discontinued and 450 ml of dimethoxyethane (DME) was slowly added to the still hot, stirred solution, resulting in the precipitation of a white solid. The solution was allowed to cool to room temperature, the solid was allowed to settle, and the supernatant was decanted from the solid. The solid was resuspended in Isopar E™ and filtered. Yield was 210 g (79 percent) of an off-white solid.

B) Preparation of (tert-butylamido )dimethyl (tetramethyl-$\eta^5$-cyclopentadienyl)silane titanium diisopropoxide In a drybox, 24.95 g of titanium tetraisopropoxide (Ti(O-$^iPr)_4$) (Aldrich Chemical Company) (88 mmol) was dissolved in about 200 ml of hexane. 58 g of solid $[Me_4C_5SiMe_2N^tBu][MgCl]_2(DME)_n$ (effective molecular weight by titration: about 629 g/mole; 92 mmol) was added to the flask, using about 50 ml of additional hexane. The mixture was stirred overnight at room temperature, then filtered through a medium porosity fritted glass filter (10–15 μm porosity). The solids remaining on the frit were washed with additional hexane until the washings were colorless. A yellow/orange solution was obtained, and the volatile materials were removed under reduced pressure to leave $(Me_4C_5SiMe_2N^tBu)Ti(O^iPr)_2$ as a yellow crystalline solid in essentially quantitative yield. $^1H$ NMR $(C_6D_6)$: 4.57 ppm (septet, 2H), 2.16 ppm (s, 6H), 1.91 ppm (s, 6H), 1.37 ppm (s, 9H), 1.15 ppm (d, 12H), and 0.65 ppm (6H).

C1) Preparation of (tert-butylamido)dimethyl (tetramethyl-$\eta^5$-cyclopentadienyl)silane titanium $\eta^4$-1,4-diphenyl-1,3-butadiene In a drybox, 0.125 g of (tert-butylamido)dimethyl(tetramethyl-$\eta^5$-cyclopentadienyl)silane titanium diisopropoxide $((Me_4C_5SiMe_2N^tBu)Ti(O^iPr)_2)$ and 0.062 g of 1,4-diphenyl-trans,trans-1,3-butadiene (purchased from Aldrich Chemical Co]) were mixed in 20 mL of anhydrous Isopar E™. To this was added 5.0 mL of a 0.015M solution of triethylaluminum in Isopar E™. The color immediately turned from very pale yellow to orange. The reaction mixture was heated with stirring to a gentle reflux. The color gradually darkened to a deep red/purple. After three hours, the solution was cooled to about 20° C. A small aliquot was removed and the volatile materials were removed under reduced pressure to leave the desired product, $(Me_4C_5SiMeN^tBu)Ti$ $CH(C_6H_5)CHCHCH(C_6H_5)$, as a purple solid. The material was identified by comparison of its $^1H$ NMR spectrum with spectra of the complex made by other routes.

C2) Preparation of (tert-butylamido)dimethyl(tetramethyl-$\eta^5$-cyclopentadienyl)silane titanium (1,3-pentadiene)

In a drybox, 0,125 g of $(Me_4C_5SiMe_2N^tBu)Ti(O^iPr)_2)$ was dissolved in 20 mL of mixed alkanes. 1,3-pentadiene (0.30 mL) was added, followed by 4.5 mL of triethylaluminum (0.15M in hexane). The color darkened slightly. The mixture was heated to reflux for 5 hours, over which time the solution color changed to deep red/brown. The solution was then cooled and a small aliquot removed and dried under reduced pressure to yield a deep red oil. The $1^H$ NMR spectrum of this material indicated that the major component was (tert-butylamido)dimethyl(tetramethyl-$\eta^5$-cyclopentadienyl)silanetitanium (1,3-pentadiene) and the minor component was (tert-butylamido)dimethyl(tetramethyl-$\eta^5$-cyclopentadienyl)silanetitanium ethylisopropoxide.

D) Polymerization

A 3.8 L stirred reactor was charged with 2 L of mixed alkane solvent (Isopar™E, available from Exxon Chemicals Inc.) and 175 mL of 1-octene comonomer. The reactor was heated to 140° C. and saturated with ethylene at 3450 Kpa. Hydrogen (Δ340 kPa) was added by differential pressure expansion from an approximately 30 mL addition tank. Catalyst/cocatalyst solutions were prepared in a drybox by combining 1.00 mL of 0.0050M solution of (tert-butylamido)dimethyl(tetramethyl-$\eta^5$-cyclopentadienyl)silane titanium $\eta^4$-1,4-diphenyl-3-butadiene (made by preparation C1) in Isopar™E, 1.50 mL of 0.0150M solution of tris(pentafluorophenyl)borane and 1.00 mL of 0.050M solution of triisobutylaluminum modified methylalumoxane in a mixture (50/50 by volume) of heptane and Isopar™E. This solution was then transferred to a catalyst addition tank and injected into the reactor.

The polymerization was allowed to proceed for ten minutes with ethylene supplied on demand. The solution was removed from the reactor and quenched with isopropanol. A hindered phenol anti-oxidant (Irganox™ 1010, available from Ciba Geigy Corp.) was added to the polymer solution. The polymer was dried in a vacuum oven set at 120° C. for about 20 hours. Yield was 127 g of ethylene/octene copolymer having a density of 0.911 g/cc, melt index, $I_2$=8.7 dg/min, and $I_{10}/I_2$=5.6.

What is claimed is:

1. A process for preparing a Group 4 metal complex corresponding to the formula:

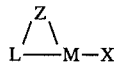

wherein:

M is titanium or zirconium in the +2 formal oxidation state;

L is a group containing a cyclic, delocalized, anionic, Π-system through which the group is bound to M;

Z is a divalent moiety bound to both L and M comprising boron, or a member of Group 14 of the Periodic Table of the Elements, and also comprising nitrogen, phosphorus, sulfur or oxygen, said moiety having up to 60 non-hydrogen atoms; and X is a neutral, conjugated or nonconjugated diene, optionally substituted with one or more hydrocarbyl groups, said X having up to 40 carbon atoms and forming a Π-complex with M;

the steps of the process comprising:

1)
 a) contacting a conjugated or nonconjugated $C_{4-40}$ diene compound with a metal complex corresponding to the formula:

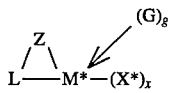

wherein,

M* is titanium or zirconium in the +3 or +4 formal oxidation state;

X* independently each occurrence is a $C_{1-20}$ hydrocarbyloxide;

x is one or two;

G is a neutral Lewis base selected from amines, phosphines and ethers said G having from 3 to 20 non-hydrogen atoms;

L and Z are as previously defined; and g is a number from 0 to 3, in an inert solvent, and b) contacting the resulting mixture with a reducing agent, or 2)
 a) contacting a conjugated or nonconjugated $C_{4-40}$ diene compound with a reducing agent in a suitable noninterfering solvent, and b) contacting the resulting mixture with a complex corresponding to the formula:

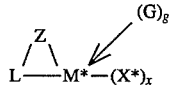

wherein,

L, Z, M*, X*, x, G and g are as previously defined.

2. A process according to claim 1 wherein X* is methoxy, ethoxy, isopropoxy, n-butoxy, or t-butoxy.

3. A process according to claim 1 wherein the hydrocarbyloxy complexes correspond to the formula:

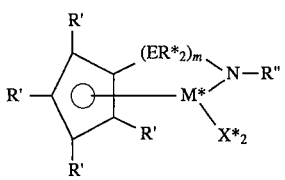

and the resulting diene containing products correspond to the formula:

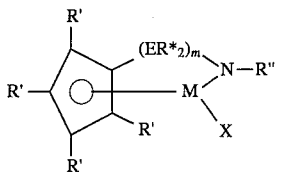

wherein

M, M*, X* and X are as previously defined in claim 1,

R* each occurrence is independently selected from the group consisting of hydrocarbyl, halohydrocarbyl, and silyl groups having up to 20 non-hydrogen atoms, and mixtures thereof;

R" is $C_{1-10}$ hydrocarbyl;

R' each occurrence is independently selected from the group consisting of hydrogen, silyl, alkyl, aryl, germyl, cyano, halo and combinations thereof having up to 20 non-hydrogen atoms, or two adjacent R' groups together form a divalent derivative thereof;

E is silicon or carbon; and m is 1 or 2.

4. A process according to claim 1 wherein the diene is 1,4-diphenyl-1,3-butadiene, 1,3-pentadiene, 1,4-dibenzyl-1,3-butadiene, 2,4-hexadiene, 3-methyl-1,3-pentadiene, 1,4-ditolyl-3-butadiene, or 1,4-bis(trimethylsilyl)-1,3-butadiene.

* * * * *

UNITED STATES PATENT AND TRADEMARK OFFICE
CERTIFICATE OF CORRECTION

PATENT NO. : 5,491,246
DATED : February 13, 1996
INVENTOR(S) : Rosen, et al

It is certified that error appears in the above-indentified patent and that said Letters Patent is hereby corrected as shown below:

Claim 1, Column 10, line 36, "the $\neq$ or +4" should correctly read --the +3 or +4--.

Signed and Sealed this

Fifth Day of October, 1999

Attest:

Q. TODD DICKINSON

Attesting Officer

Acting Commissioner of Patents and Trademarks